(12) United States Patent
Herrmann et al.

(10) Patent No.: US 7,998,129 B2
(45) Date of Patent: Aug. 16, 2011

(54) DEVICE FOR FACILITATING CARDIOPLEGIA DELIVERY IN PATIENTS WITH AORTIC INSUFFICIENCY

(75) Inventors: Howard C Herrmann, Philadelphia, PA (US); Y Joseph Woo, Lafayette Hill, PA (US)

(73) Assignee: The Trustees Of The University Of Pennsylvainia, Philadelphia, PA (US)

( * ) Notice: Subject to any disclaimer, the term of this patent is extended or adjusted under 35 U.S.C. 154(b) by 733 days.

(21) Appl. No.: 10/591,963

(22) PCT Filed: Mar. 10, 2005

(86) PCT No.: PCT/US2005/008000
§ 371 (c)(1),
(2), (4) Date: May 15, 2007

(87) PCT Pub. No.: WO2005/086926
PCT Pub. Date: Sep. 22, 2005

(65) Prior Publication Data
US 2007/0287990 A1 Dec. 13, 2007

Related U.S. Application Data

(60) Provisional application No. 60/552,342, filed on Mar. 11, 2004.

(51) Int. Cl.
*A61M 31/00* (2006.01)
*A61M 37/00* (2006.01)
(52) U.S. Cl. .................................. 604/509; 604/103.14
(58) Field of Classification Search .................. 604/509, 604/510, 43, 98.02, 164.01, 164.03, 164.1, 604/164.11, 500, 508, 99.01, 103, 103.07, 604/103.11, 103.14
See application file for complete search history.

(56) References Cited

U.S. PATENT DOCUMENTS

| | | | | |
|---|---|---|---|---|
| 5,013,296 A | * | 5/1991 | Buckberg et al. | 604/44 |
| 5,458,574 A | | 10/1995 | Machold et al. | 604/101 |
| 6,090,096 A | | 7/2000 | St. Goar et al. | 604/509 |
| 6,117,105 A | | 9/2000 | Bresnaham et al. | 604/96.01 |
| 6,149,578 A | | 11/2000 | Downey et al. | 280/293 |
| 6,159,178 A | | 12/2000 | Sharkawy et al. | 604/103.08 |
| 6,176,851 B1 | | 1/2001 | Tsugita et al. | 604/509 |
| 6,231,544 B1 | | 5/2001 | Tsugita et al. | 604/104 |
| 6,267,747 B1 | * | 7/2001 | Samson et al. | 604/103.07 |
| 6,638,293 B1 | * | 10/2003 | Makower et al. | 606/200 |
| 6,673,040 B1 | | 1/2004 | Samson et al. | 604/101.01 |
| 2003/0138350 A1 | | 7/2003 | MacOviak et al. | 422/45 |

* cited by examiner

*Primary Examiner* — Theodore J Stigell
*Assistant Examiner* — Bradley J Osinski
(74) *Attorney, Agent, or Firm* — Woodcock Washburn, LLP

(57) ABSTRACT

A method and device that addresses the problem of an incompetent aortic valve by using a simple cardioplegia catheter that can deliver cardioplegia solution to the coronary arteries through the usual aortic cannulation site even in the presence of aortic valve incompetence. The device includes a cardioplegia cannula (32) with an additional lumen containing a nitinol wire (34) inside it that allows advancement of a folded nitinol umbrella (36) with a non-porous membrane or a compressed nitinol ring that covers the aortic valve when opened. During installation, after puncture of the aorta by the coaxial needle and removal of the coaxial needle but before installation of the cardioplegia solution through the central lumen of the catheter, the nitinol umbrella (in folded position) or nitinol ring (in compressed position) is advanced through the second lumen into the aorta just above the aortic valve. The nitinol umbrella is unfolded using the nitinol wire to expose the inverted umbrella configuration with attached membrane and is then advanced as a unit with the cardioplegia catheter until the nitinol umbrella covers the aortic valve at its deployed position.

7 Claims, 2 Drawing Sheets

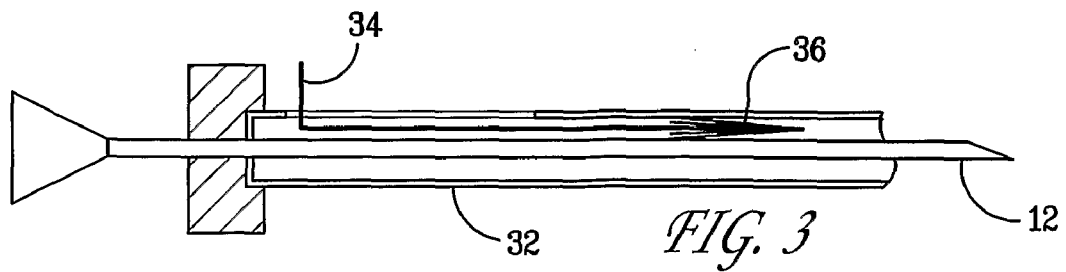
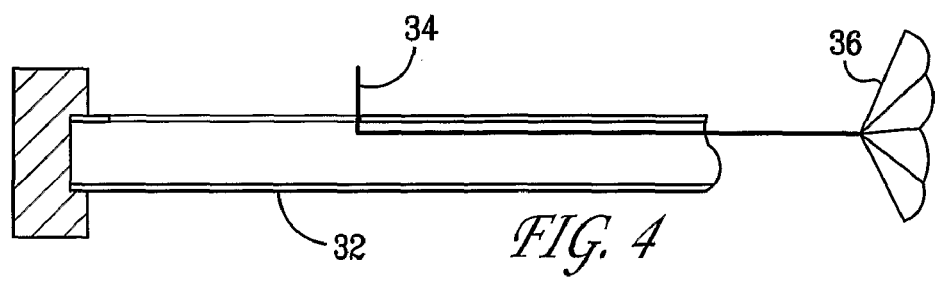
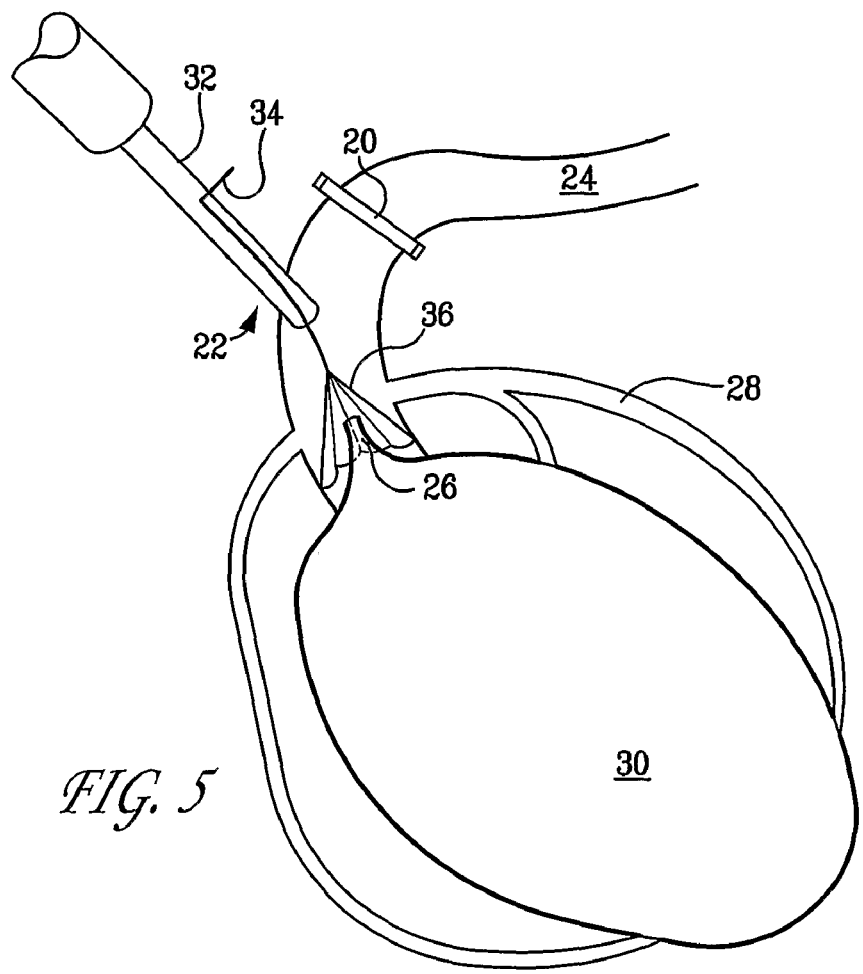

DEVICE FOR FACILITATING CARDIOPLEGIA DELIVERY IN PATIENTS WITH AORTIC INSUFFICIENCY

CROSS-REFERENCE TO RELATED APPLICATIONS

This application is the National Stage of International Application No. PCT/US2005/008000, filed Mar. 10, 2005, which claims the benefit of U.S. provisional Application No. 60/552,342, filed Mar. 11, 2004, the disclosure of which is incorporated herein by reference in its entirety.

FIELD OF THE INVENTION

The present invention relates to a device to facilitate cardioplegia administration by preventing the cardioplegia from leaking through the aortic valve into the left ventricle.

BACKGROUND OF THE INVENTION

Prior art devices address particular issues in open-heart surgery such as how to occlude the aorta while on cardiopulmonary bypass (CPB). There are two aspects of such devices that involve the aorta during CPB. One is to occlude the aorta to allow the pump to perfuse the body without entering the left ventricle or ascending aorta. This is usually accomplished with a clamp (called a cross-clamp) placed across the ascending aorta above the coronary ostia. Many of the prior art devices provide alternate ways to accomplish this occlusion from inside the aorta, for example, with a balloon directly inserted or passed intravascularly as a catheter. The second important part of CPB involves administering the cardioplegia in the ascending portion of the aorta below the cross clamp where it is trapped between the cross clamp and the aortic valve forcing it down the coronary arteries to protect the myocardium during heart stoppage. Prior art methods are known for administering the cardioplegia and clamping or occluding the aorta. Examples of such prior art devices are provided in the following patents.

U.S. Pat. No. 6,267,747 (Samson et al.) discloses an aortic catheter system having an aortic root balloon that occludes the aorta for the delivery of cardioplegia during cardiopulmonary bypass and may be used to help maintain the competency of regurgitant aortic valves. The balloon occluder described by Samson et al. is inserted from the groin to allow occlusion of the ascending aorta and to block the aortic valve. Samson et al. disclose the use of a porous aortic root balloon that is capable of occluding the aorta, delivering cardioplegia, providing tactile feedback, and helping to maintain the competency of regurgitant aortic valves. With respect to FIG. 12, Samson et al. describe that the most distal balloon may conform to the cusps of the aortic valve to prevent cardioplegia from entering the ventricle through the aortic valve. Samson et al. also disclose that any desirable or practical collapsible valve may be used; however, Samson et al. do not describe the use of a foldable umbrella type device that may be delivered through the aortic root via a standard cardioplegia cannula for deployment at the aortic valve.

U.S. Pat. No. 6,673,040 (Samson et al.) discloses the placement of umbrella type flow control valves in the aorta for arterial perfusion during non-surgical procedures. Generally, Samson et al. teach placing inflatable occlusion balloons in the patient's ascending aorta between the coronary arteries and the brachiocephalic artery. Again, no umbrella type device inserted through the aortic root via a standard cardioplegia cannula is taught.

U.S. Pat. No. 6,090,096 (St. Goar et al.) also disclose a catheter balloon occlusion system, in this case inserted from the left atrium to the ascending aorta to occlude the aorta as a cross clamp would above the coronary ostia. The occlusion member may alternatively be a collapsible one-way valve with one or more movable leaflets, an umbrella-like expanding membrane, or other mechanical occlusion device. However, the device disclosed by St. Goar is not used for valve blockage but, instead, the balloon is used to occlude the ascending aorta between the brachiocephalic artery and the coronary ostia. The catheter itself is introduced through the wall of the heart into the left atrium, advanced through the mitral valve, and into the ascending aorta.

U.S. Pat. No. 5,458,574 (Machold et al.) discloses a similar system to the St. Goar et al. occlusion system for isolating the coronary arteries using a catheter with two expandable occlusion devices during cardiopulmonary bypass.

U.S. Pat. No. 6,638,293 (Makower et al.) discloses an umbrella-type embolic device for occluding the ascending aorta. Makower et al. do not teach blocking flow in the aorta across the aortic valve.

Other techniques are known in the art for aortic occlusion above the aortic valve (cross clamp equivalents). For example, U.S. Pat. No. 6,231,544 (Tsugita et al.) discloses a cardioplegia balloon cannula for aortic occlusion and filtering with a "cape" cannula, while U.S. Pat. No. 6,176,851 (Tsugita et al.) discloses a cardioplegia occluder which opens downstream from a solution introducing port to isolate the aorta from other vasculature. U.S. Pat. No. 6,159,178 (Sharkawy et al.) further discloses methods and devices for occluding the ascending aorta and delivering cardioplegic fluid to arrest the heart, while U.S. Pat. No. 6,149,578 (Downey et al.) discloses an expandable device for occluding the ascending aorta. U.S. Pat. No. 6,117,105 (Bresnaham et al.) discloses an aortic catheter including valve occlusion members deployed adjacent the aortic valve.

However, the devices of these prior art patents address a separate problem to that addressed by the device described herein. As will be explained below, the present invention addresses the situation where the aortic valve is not fully competent. In this setting, administration of the cardioplegia to the ascending aorta can enter the left ventricle below the coronary arteries where it causes two problems: (1) expansion of the left ventricular size which increases oxygen demand and (2) less cardioplegia goes into the coronary arteries. The net effect is inadequate myocardial protection during the operation. The present invention addresses this separate problem in the art.

SUMMARY OF THE INVENTION

The present invention relates to a technique and associated device for blocking the cardioplegia from crossing the aortic valve and better "trapping" it between the valve and the cross clamp, thereby forcing it down the coronary arteries. The present invention does not address the exact method of administration of the cardioplegia or provide a method to cross clamp or obstruct the aorta above the coronary arteries. Instead, a device is described that prevents the cardioplegia from leaking through an incompetent aortic valve into the left ventricle.

The present invention addresses the problem of an incompetent aortic valve by using a simple cardioplegia catheter that can deliver cardioplegia solution to the coronary arteries through the usual aortic cannulation site even in the presence of aortic valve incompetence. A cardioplegia cannula is provided with an additional lumen containing a nitinol wire inside it that allows advancement of a folded nitinol umbrella or nitinol ring with a non-porous membrane designed to cover the aortic valve when the nitinol umbrella or nitinol ring is opened. After puncture of the aorta by the coaxial needle and removal of the coaxial needle but before installation of the cardioplegia solution through the central lumen of the catheter, the nitinol umbrella (in folded position) or nitinol ring (in collapsed position) is advanced through the second lumen into the aorta just above the aortic valve. The nitinol umbrella or nitinol ring is unfolded to expose the inverted umbrella configuration with attached membrane or the opened nitinol ring and is then advanced as a unit with the cardioplegia catheter until the nitinol umbrella or nitinol ring covers the aortic valve at its deployment position. The deployed umbrella or ring prevents cardioplegia from passing through an incompetent aortic valve to the left ventricle.

The nitinol umbrella or nitinol ring may be replaced by other physical devices that may be advanced through the cardioplegia catheter and deployed so as to occlude the aortic valve during cardioplegia installation. These and other such embodiments will be apparent to those skilled in the art from the following detailed description.

BRIEF DESCRIPTION OF THE DRAWINGS

A method and apparatus for occluding an aortic valve in accordance with the invention will be apparent to those skilled in the art based on the following disclosure, of which:

FIG. 3 illustrates a cardioplegia cannula in accordance with the invention having an additional lumen containing a nitinol wire inside it that allows advancement of a folded nitinol umbrella with a non-porous membrane that covers the aortic valve when the nitinol umbrella is opened.

FIG. 4 illustrates the cardioplegia cannula of FIG. 3 where the nitinol umbrella is unfolded.

FIG. 5 illustrates the nitinol umbrella of FIGS. 3 and 4 at its deployment position where it covers the aortic valve.

DETAILED DESCRIPTION OF ILLUSTRATIVE EMBODIMENTS

A detailed description of an illustrative embodiment of the present invention will now be described with reference to FIGS. 1-5. Although this description provides detailed examples of possible implementations of the present invention, it should be noted that these details are intended to be exemplary and in no way delimit the scope of the invention. The scope of the invention is delimited by the appended claims.

The present invention relates to a device to facilitate cardioplegia administration. During open-heart surgery utilizing cardiopulmonary bypass (whether traditional or minimally invasive), the heart must be stopped and the myocardium preserved. This is accomplished by administering a solution that contains high potassium to stop electrical conduction in the heart (to reduce metabolic demand), nutrients to allow the myocardial cells to have an energy source, and a combination of cardioprotective substances (including cold temperature) to reduce myocardial cell metabolism during the period of interrupted coronary blood flow (which normally supplies oxygen and nutrients for the metabolizing cells). This solution is called cardioplegia.

Figure 1:
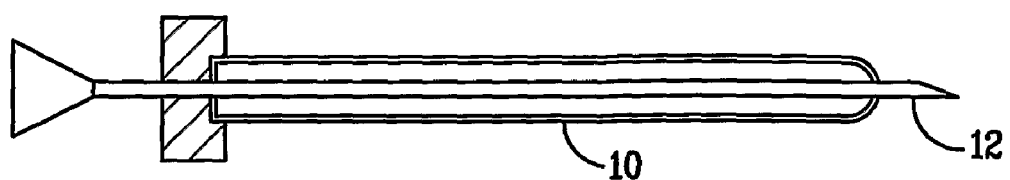
FIG. 1 illustrates a conventional cardioplegia aortic root cannula with a lumen designed to accept a catheter with a coaxial needle inserted therethrough to puncture the aorta.
Figure 2:
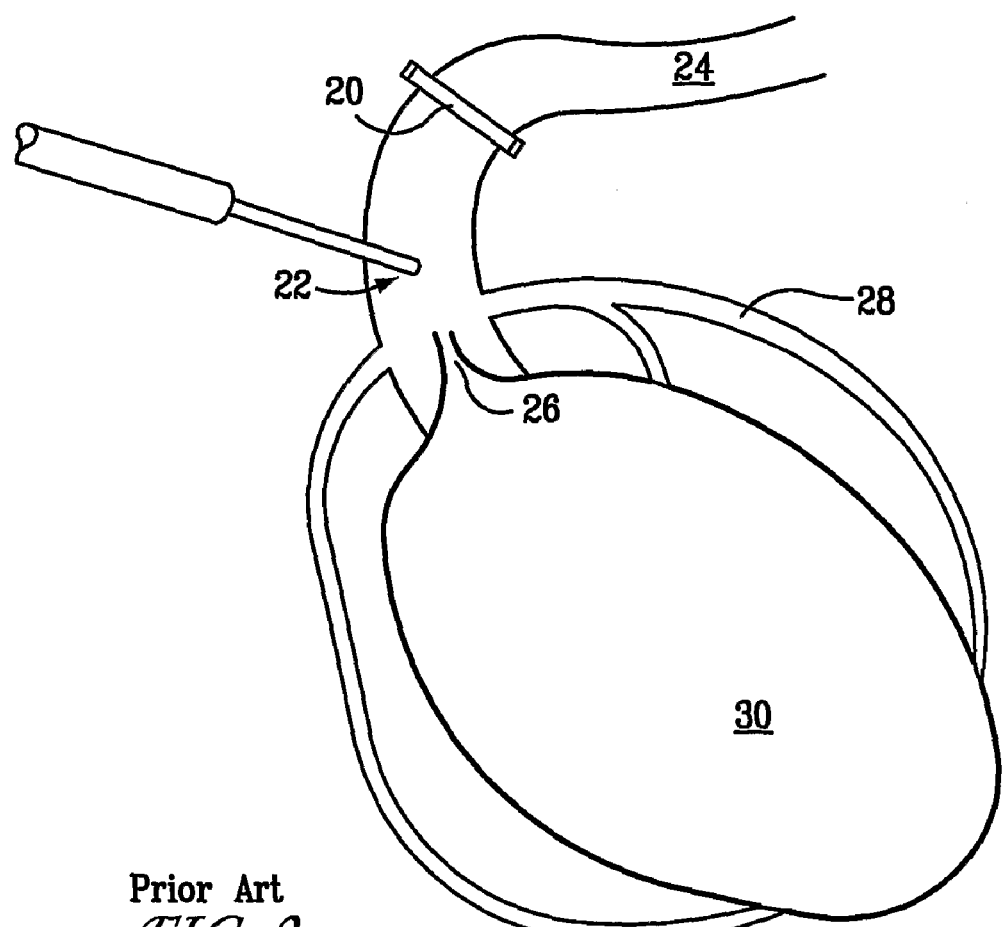
FIG. 2 illustrates conventional administration of the cardioplegia at a cannulation site between the cross-clamp and the aortic valve so as to force the infusing solution into the ascending aorta where it is trapped between the aortic valve and the cross-clamp.

The cardioplegia solution is usually administered through the ascending aorta via a cannula ("root cardioplegia"). As shown in FIG. 1, such a cardioplegia aortic root cannula generally includes a catheter 10 with a coaxial needle 12 inserted therethrough to puncture the aorta for insertion. As shown in FIG. 2, during administration of the cardioplegia, a clamp (cross-clamp) 20 is placed above the cannulation site 22 in order to force the infusing solution into the ascending aorta 24 where it is trapped between the aortic valve 26 and the cross-clamp 20. The coronary arteries 28 arise in this location (just above the aortic valve 26) and the cardioplegia solution therefore flows down the coronary arteries 28 to the cardiac muscle cells. Unfortunately, many patients have some degree of aortic valve incompetence (also called aortic insufficiency or aortic regurgitation). In these patients, the cardioplegia solution can enter the left ventricle 30 through the aortic valve 26, which has several deleterious effects. First, inadequate myocardial protection may occur due to the lack of cardioplegia down the coronary arteries 28. Second, the left ventricle 30 can dilate due to the volume of fluid thereby raising the myocardial oxygen demands of the myocardial cells (via LaPlace's law). In addition, displacement of the aortic valve leaflets during the heart operation as a result of manipulating or torquing of the heart, mitral valve operations, and other minimally invasive procedures, may result in the production of aortic insufficiency and lead to inadequate cardioplegia.

The surgeon has several options to deal with the above scenario, including placing the cardioplegia solution via selective catheters directly into the ostia of the left and right coronary arteries. This is not totally satisfactory because it requires opening the aorta more fully to directly visualize the coronary ostia (increases the time for the operation, requires later repair of the aorta, increases the risk for complications related to the aortic suture line, and poses a small risk of injuring the main coronary ostia). Alternatively, the surgeon can attempt other modes of myocardial protection (retrograde via the coronary sinus, etc.). However, retrograde cardioplegia via the coronary sinus has may disadvantages, including the potential to occlude right ventricular venous drainage. Root cardioplegia is most physiologic, the most commonly utilized, and is associated with the fewest complications.

The present invention addresses the problem of an incompetent aortic valve by using a simple cardioplegia catheter that can deliver cardioplegia solution to the coronary arteries 28 through the usual aortic cannulation site 22 even in the presence of aortic valve incompetence. As shown in FIG. 3, the invention includes a cardioplegia cannula 32 with an additional lumen containing a nitinol wire 34 inside it that allows advancement of a folded nitinol umbrella 36 with a non-porous membrane that covers the aortic valve 26 when the nitinol umbrella 36 is opened as shown in FIG. 4. After puncture of the aorta by the coaxial needle 12 and removal of the coaxial needle 12 but before installation of the cardioplegia solution through the central lumen of the catheter 32, the nitinol umbrella 36 (in folded position) is advanced through the second lumen into the aorta just above the aortic valve. The nitinol umbrella 36 is unfolded using the nitinol wire 34 to expose the inverted umbrella configuration with attached membrane as shown in FIG. 4 and is then advanced as a unit with the cardioplegia catheter until the nitinol umbrella 36 covers the aortic valve 26 at its deployment position shown in FIG. 5. During installation of the cardioplegia solution (after aortic cross clamping), the solution is trapped above the membrane 26, below clamp 20, and forced down the coronary arteries 28 regardless of whether the aortic valve 26 is closed, open, normal, or incompetent.

Those skilled in the art will appreciate that the nitinol umbrella 36 may be replaced by a nitinol ring that may be compressed to travel through the catheter lumen and that springs open when it emerges from the distal end of the catheter lumen for deployment over the aortic valve 26. Similarly, a disc shaped or flat balloon occluder or any other appropriate non-porous mechanical device that may be advanced through a lumen of the catheter 32 and opened for deployment through conventional inflation techniques so as to occlude the ascending aorta just above the aortic valve but below the coronary ostia may be used. In the case of a balloon occluder, a lumen just above the balloon would be used to allow installation of the cardioplegia solution. Such an arrangement would still block retrograde flow through an incompetent aortic valve while delivering the cardioplegia solution.

Those skilled in the art will appreciate that other modifications to the aortic valve occluding device of the invention may be implemented by those skilled in the art without deviating from the inventive principles of the invention. Accordingly, any such modifications are intended to be included within the scope of this invention as defined by the following exemplary claims.

What is claimed:

1. A method of delivering cardioplegia solution to the coronary arteries even in the presence of aortic valve incompetence, comprising the steps of:
    puncturing the ascending aorta at a puncture position between a cross-clamp above the coronary arteries and the left ventricle using a coaxial needle inserted through a lumen of a cardioplegia cannula;
    removing the coaxial needle from the cardioplegia cannula;
    inserting the cardioplegia cannula into the ascending aorta at the puncture position, the cannula including at least one lumen for cardioplegia delivery and for accepting a folded non-porous membrane that is adapted to cover the aortic valve when opened;
    inserting a folded membrane into the at least one lumen and advancing the folded membrane until the membrane is within the ascending aorta just above the aortic valve;
    opening the membrane upon emergence from a distal end of the lumen and advancing the opened membrane away from the distal end of the lumen until it covers the aortic valve at a deployment position below the coronary arteries; and
    inserting the cardioplegia solution into the first lumen, whereby the membrane prevents the cardioplegia solution from entering the left ventricle through the aortic valve and the membrane traps the cardioplegia solution above the membrane and below the cross-clamp so as to force the cardioplegia solution down the coronary arteries.

2. A method as in claim 1, wherein the membrane is an umbrella and said opening step comprises opening the membrane using a wire that is inserted into the at least one lumen.

3. A method as in claim 1, wherein the membrane is a nitinol ring that is compressed for insertion into the at least one lumen and said opening step comprises pushing the membrane through the lumen until it springs open when it emerges from the distal end of the lumen.

4. A cardioplegia cannula for delivering cardioplegia solution to the coronary arteries even in the presence of aortic valve incompetence, comprising:
    an elongated tube comprising at least one lumen adapted to accept a coaxial needle for puncturing the ascending aorta at a puncture position between a cross-clamp above the coronary arteries and the left ventricle, and said at least one lumen being adapted for cardioplegia delivery; and
    a foldable non-porous membrane that is adapted to advance through said at least one lumen, through the puncture site and into said ascending aorta, said membrane adapted to open upon emergence from a distal end of the lumen and to advance away from the distal end of the lumen so as to cover the aortic valve at a deployment position below the coronary arteries when opened whereby, when deployed, the membrane prevents the cardioplegia solution from entering the left ventricle through the aortic valve when the cardioplegia solution is inserted into the ascending aorta via the at least one lumen and the membrane traps the cardioplegia solution above the membrane and below the cross-clamp so as to force the cardioplegia solution down the coronary arteries.

5. A cardioplegia cannula as in claim 4, wherein the membrane is an umbrella that is opened using a wire that is inserted into the at least one lumen.

6. A cardioplegia cannula as in claim 5, wherein the umbrella and the wire are made of nitinol.

7. A cardioplegia cannula as in claim 4, wherein the membrane is a nitinol ring that may be compressed for insertion into the at least one lumen and that is adapted to spring open when it emerges from distal end of the lumen.

* * * * *